(12) United States Patent
Jenkins et al.

(10) Patent No.: US 7,096,070 B1
(45) Date of Patent: Aug. 22, 2006

(54) MEDICAL IMPLANT DEVICE FOR ELECTROSTIMULATION USING DISCRETE MICRO-ELECTRODES

(75) Inventors: David Jenkins, Flanders, NJ (US); Pat Gordon, Wayzata, MN (US)

(73) Assignee: Transneuronix, Inc., Mount Arlington, NJ (US)

( * ) Notice: Subject to any disclaimer, the term of this patent is extended or adjusted under 35 U.S.C. 154(b) by 940 days.

(21) Appl. No.: 09/777,979

(22) Filed: Feb. 6, 2001

Related U.S. Application Data

(60) Provisional application No. 60/249,654, filed on Nov. 17, 2000, provisional application No. 60/249,096, filed on Nov. 15, 2000, provisional application No. 60/181,320, filed on Feb. 9, 2000.

(51) Int. Cl.
*A61N 1/00* (2006.01)

(52) U.S. Cl. ............ 607/116; 607/148; 600/373; 600/377; 128/898

(58) Field of Classification Search .......... 607/116–117, 607/119, 122, 9, 148; 600/373–374, 377, 600/393; 128/898
See application file for complete search history.

(56) References Cited

U.S. PATENT DOCUMENTS

| | | | |
|---|---|---|---|
| 2,865,376 A | 12/1958 | Pellier et al. | |
| 3,760,812 A | 9/1973 | Timm et al. | |
| 4,444,207 A | 4/1984 | Robicsek | |
| 4,475,560 A | 10/1984 | Tarjan et al. | |
| 4,524,771 A | 6/1985 | McGregor et al. | |
| 4,549,556 A | 10/1985 | Tarjan et al. | |
| 4,557,271 A * | 12/1985 | Stoller et al. | 128/734 |
| 4,901,722 A | 2/1990 | Noguchi | |
| 5,059,207 A | 10/1991 | Shah | |
| 5,100,431 A | 3/1992 | Buster et al. | |
| 5,121,754 A | 6/1992 | Mullett | |
| 5,217,471 A | 6/1993 | Burkhart | |
| 5,230,337 A * | 7/1993 | Dahl et al. | 607/5 |
| 5,242,458 A | 9/1993 | Bendel et al. | |
| 5,292,344 A | 3/1994 | Douglas | |
| 5,423,872 A | 6/1995 | Cigaina | |
| 5,423,876 A | 6/1995 | Camps et al. | |
| 5,433,728 A | 7/1995 | Kim | |
| 5,450,739 A | 9/1995 | Bogart et al. | |
| 5,489,294 A | 2/1996 | McVenes et al. | |

(Continued)

FOREIGN PATENT DOCUMENTS

DE  44 02 058  1/1994

(Continued)

*Primary Examiner*—Frederick C. Nicolas
(74) *Attorney, Agent, or Firm*—Fitch, Even, Tabin & Flannery

(57) ABSTRACT

An improved medical implant device is provided which has a plurality of micro-electrodes. The use of a plurality of micro-electrodes allows a clinically effective electrical stimulation pathway to be selected once the implant is positioned within or adjacent to the tissue to be treated even if the implant is not optimally placed or located. Thus, in cases where the implant is not optimally placed, it is not necessary to remove the implant and then reposition it within or adjacent to the tissue to be treated, thereby reducing stress to the patient caused by additional surgery. Moreover, using the micro-electrodes of this invention, directional electrostimulation can be provided to the tissue to be treated. Implant devices with a plurality of micro-electrodes are provided which are especially adapted for use in reducing the frequency and/or severity of neurological tremors. Other implant devices having micro-electrodes are provided which are especially adapted for electrostimulation and/or electrical monitoring of endo-abdominal tissue or viscera.

36 Claims, 5 Drawing Sheets

U.S. PATENT DOCUMENTS

| | | | |
|---|---|---|---|
| 5,515,848 A | 5/1996 | Corbett, III et al. | |
| 5,630,839 A * | 5/1997 | Corbett, III et al. | 607/137 |
| 5,690,691 A | 11/1997 | Chen et al. | |
| 5,715,821 A * | 2/1998 | Faupel | 128/653.1 |
| 5,716,392 A | 2/1998 | Bourgeois et al. | |
| 5,800,500 A * | 9/1998 | Spelman et al. | 607/137 |
| 5,836,994 A | 11/1998 | Bourgeois | |
| 5,843,147 A * | 12/1998 | Testerman et al. | 607/116 |
| 5,861,014 A | 1/1999 | Familoni | |
| 5,913,882 A * | 6/1999 | King | 607/62 |
| 5,928,269 A * | 7/1999 | Alt | 607/5 |
| 5,995,872 A | 11/1999 | Bourgeois | |
| 6,011,996 A * | 1/2000 | Gielen et al. | 607/116 |
| 6,104,960 A * | 8/2000 | Duysens et al. | 607/117 |
| 6,146,391 A | 11/2000 | Cigaina | |
| 6,165,180 A * | 12/2000 | Cigaina et al. | 607/108 |
| 6,246,912 B1 * | 6/2001 | Sluijter et al. | 607/100 |
| 6,425,877 B1 * | 7/2002 | Edwards | 604/21 |
| 6,477,423 B1 * | 11/2002 | Jenkins | 607/40 |

FOREIGN PATENT DOCUMENTS

| | | |
|---|---|---|
| WO | WO 97/41921 | 11/1997 |
| WO | WO 98/53878 | 12/1998 |

* cited by examiner

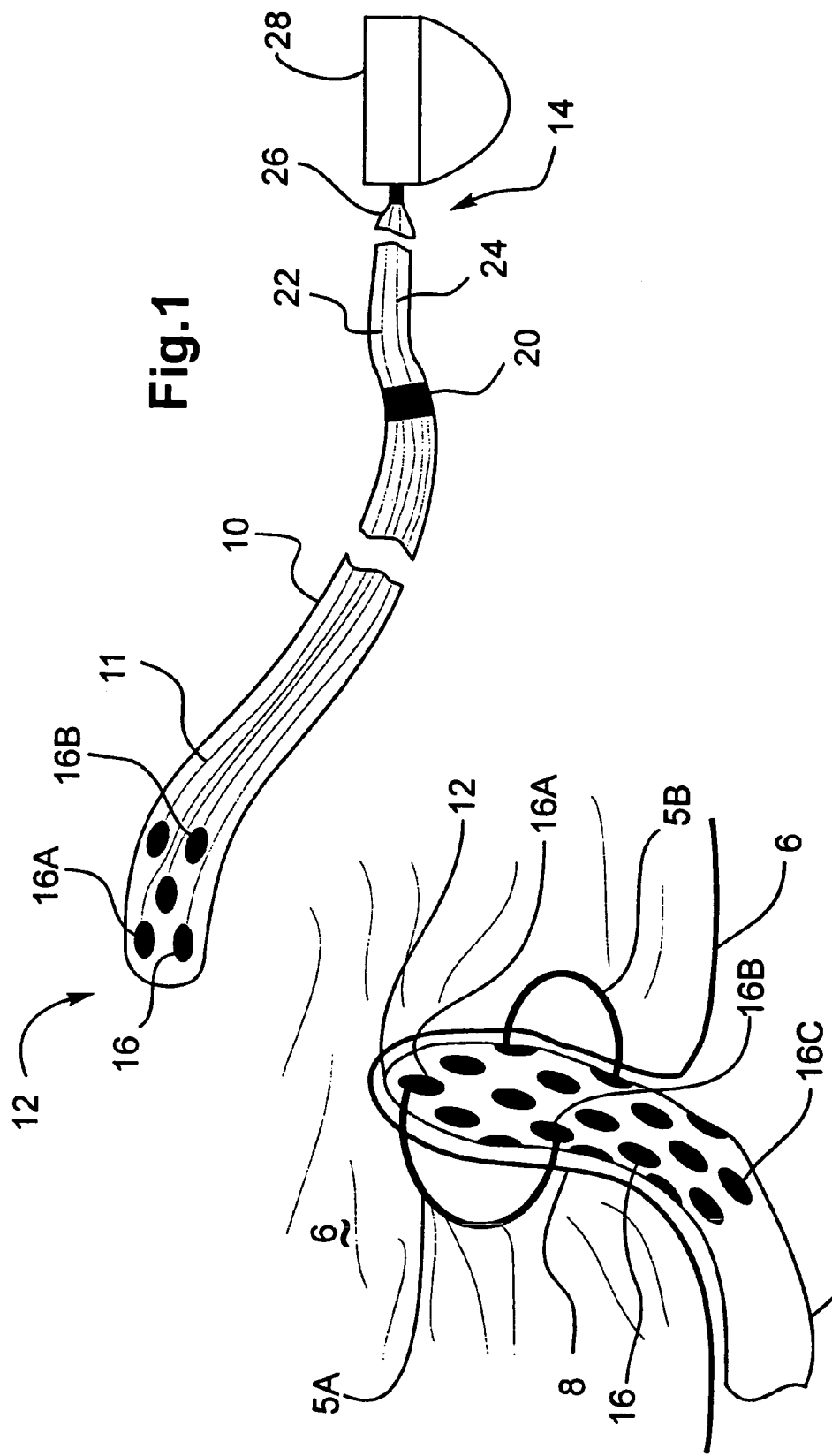

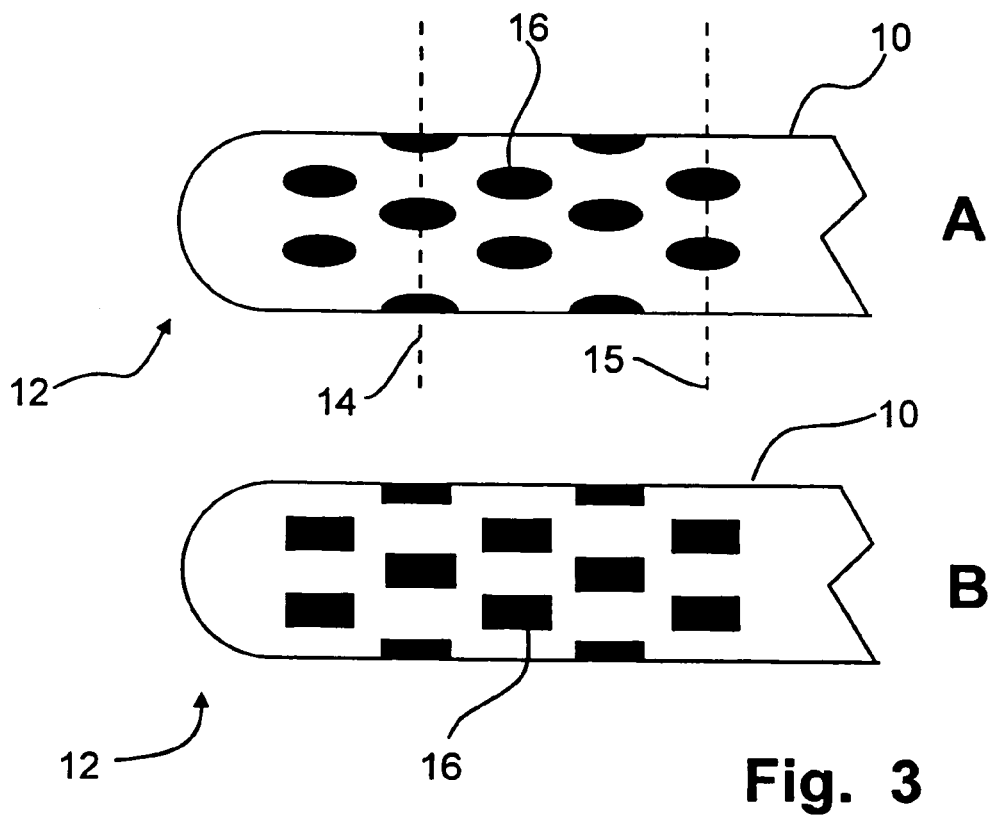
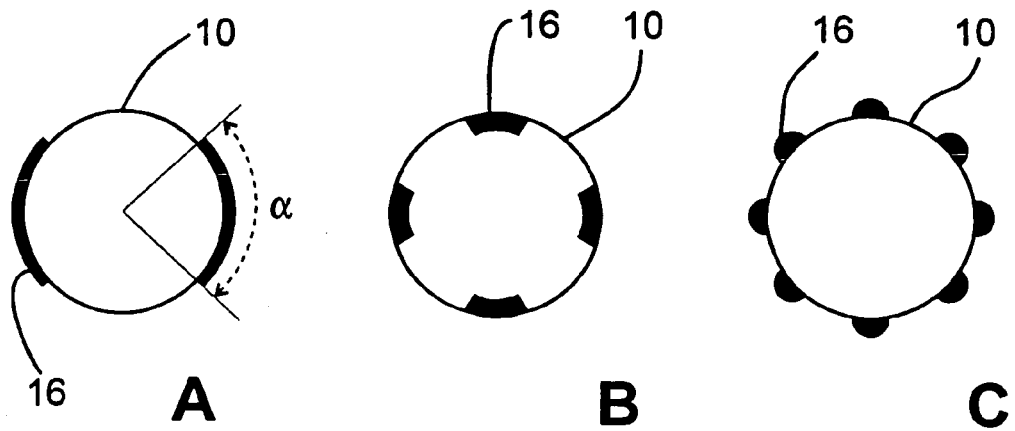

MEDICAL IMPLANT DEVICE FOR ELECTROSTIMULATION USING DISCRETE MICRO-ELECTRODES

RELATED APPLICATIONS

This application is based on, and claims benefit of Provisional Application Ser. Nos. 60/181,320, filed Feb. 9, 2000; 60/249,096, filed Nov. 15, 2000; and 60/249,654, filed Nov. 17, 2000.

FIELD OF THE INVENTION

This invention relates to a medical implant device which is designed and adapted for electrostimulation and/or electrical monitoring of internal tissue or organs in mammals and especially in humans. This medical implant device is especially adapted for electrostimulation and/or electrical monitoring of neuroglial or neuro-muscular tissue (including brain tissue) or endo-abdominal tissue or viscera. This medical implant device can be used in laparoscopic surgery or other surgical or microsurgical techniques. This medical implant device comprises an elongated body having a plurality of discrete micro-electrodes that are electrically connected to an electric connection terminal for connection to a power source, such that any two of the discrete micro-electrodes can potentially be used for establishing the electrical pathway. In one preferred embodiment, the medical implant device is a pacemaker system having an implantable medical device with discrete micro-electrodes designed and adapted for electrostimulation and/or electrical monitoring of neurological and neuro-muscular tissue, including brain tissue, in a mammal. In another preferred embodiment, the elongated body is equipped with immobilizing or securing devices to secure it to the tissue or organ (e.g., endo-abdominal tissue or viscera) to be treated, a plurality of discrete micro-electrodes that are electrically connected to an electric connection terminal for connection to a power source, such that any two of the discrete micro-electrodes can potentially be used for establishing the electrical pathway, a mechanism to penetrate the tissue or organ to be treated, and quick-release connecting devices to separate the penetration device from the elongated body. This invention is also related to an improved method for electrostimulation of tissue using the medical implant devices of this invention.

BACKGROUND OF THE INVENTION

Recently, neurological stimulation has received increased interest as a medical tool for providing electrostimulation of brain tissue, especially deep brain tissue, in an effort to provide therapeutic benefit for patients suffering from various brain disorders. Such neurological stimulation has been used, for example, to control epileptic seizures and tremors associated with Parkinson and other brain diseases. Generally such medical systems include an implantable pulse generator (i.e., pacemaker), an elongated body with electrodes on the distal end which is implanted in the brain (typically in the region of the thalamus), and a connector on the proximal end to electrically connect the electrodes to the pacemaker.

The current implant procedures are performed in a surgical setting using stereo tactic techniques. The target area within the brain is generally identified using, for example, magnetic resonance imaging, computer tomography, or ventriculography. Once the implantable device is advanced to the target area, electrical stimulation tests are conducted to confirm the ideal site for embedding the electrode and for determining the pacing parameters suitable for good tremor suppression. In some cases, two implantable devices, each with its own pacing parameters, are implanted for bilateral stimulation of the thalamus region to control bilateral tremors.

Placement of the electrodes within the brain is generally not as precise as desired. Since the electrodes may not be placed properly, the desired tremor control may not be affected. In that case, the implant device and its electrodes may need to be relocated, thereby subjecting the brain tissue to increased risk of damage. To at least partially remedy this situation, four electrodes, each formed by a metal band surrounding the entire circumference of the device, have been used. Any combination of the four electrodes can be used for electrical stimulation by using any one electrode to deliver the electrical pulse and any other of the remaining electrodes to provide the return path. Using appropriate software, the pacemaker can be switchable and programable so that the appropriate combination of electrodes can be used. Using such systems, the pacing current or voltage is applied to, and absorbed by, tissue surrounding the electrode throughout the entire 360° circumference. Although this present system does allow control through the selection of the two electrodes (out of the four electrodes available) to form the pacing circuit, further control and precision with regard to electrode placement relative to the tissue to be treated would be desirable. Moreover, this arrangement does not allow directional electrostimulation.

Medical implant devices are also used for electrostimulation and/or monitoring of other tissue, including, for example, tissue and/or viscera of the gastrointestinal tract. It is well known that more than 70% of illnesses affecting the digestive tract are of a functional nature. Today such illnesses are treated predominantly using pharmacological means. Since drugs generally have side effects, particularly when the drugs cure the symptom and not the underlying problem or dysfunction, they must often be administered temporally. Indeed, if the side effects are sufficiently serious, the drug may have to be discontinued before full benefit to the patient is realized; in many cases the underlying illness remains.

The important role played by electrophysiology in controlling gastrointestinal activity has become increasingly apparent in recent years. Thus, the possibility exists of correcting dysfunction by means of electrostimulation applied at specific frequencies, sites, and modalities and with regard to the self-regulating electromotor physiology of the gastrointestinal organs or tract. It has recently been shown, for example, that changes occur in the motility and electromotor conduct of the gastric tract in eating disorders (e.g., obesity, thinness, bulimia, anorexia). Disturbances in electromotor activity in diabetic gastroparesis, reflux in the upper digestive tract, and numerous other gastroenterological functional pathologies have also been observed.

Stimulation of the intrinsic nervous system of the stomach is likely to have two major consequences or effects: (1) the correction and direct control of the electromotor activity of the intestines and (2) the stimulation of increased incretion of specific substances (i.e., gastroenteric neuromediators) produced by the intrinsic nervous system. Curing of functional illnesses involving the digestive system and, more broadly, involving disorders in any way connected to, or associated with, the digestive system is, therefore, closely linked to the progress of research in the field of electrophysiology.

An indispensable condition for modifying the electrical activity of the digestive system's intestinal tract and related neurohormonal incretions is the use of an implant system to generate electrical impulses (electrical stimuli) and means (e.g., electrocatheters) to connect them to the viscera and/or intestines to be stimulated. These treatment methods involve an "invasive" surgical technique to implant the electrocatheter in the abdomen. This may involve open or, preferably, micro-invasive surgery (i.e., video-laparoscopic surgery). Current electrocatheters to stimulate electrically and/or monitor endo-abdominal viscera may have metal microbarbs which are angled in such a way as to permit application of the end of the catheter and to prevent it subsequently from being dislodged. However, metal microbarbs can damage surrounding tissue especially when exposed to the vigorous action of the digestive tissue and/or organs. Among the undesirable consequences of such damage is erosion of the electrode into the lumen of the gastrointestinal tract. This would result in contamination of the abdominal cavity and the electrode. The subsequent infection would, at a minimum, require removal of the catheter and involve an additional operation.

During laparoscopic procedures, after administering a general anesthetic, the patient's abdomen is inflated with $CO_2$ or another inert inflammable gas, thereby transforming the abdominal cavity from a virtual to a real cavity. Rigid tubes with air-tight valve mechanisms ("trocars") are then inserted into the gas-filled abdominal cavity so that a video camera and other surgical instruments can be introduced into the abdomen. The operation then proceeds by viewing the video images transmitted by the camera. Multiple trocars are required. Generally, the first trocar provides access to the abdomen by the video camera in order to monitor the surgical procedure. A clamp is normally inserted in the second trocar to move or retain the hepatic edge that normally covers the lesser curve of the stomach or other viscera depending on the type of operation to be performed. A third trocar provides access for a maneuvering clamp or laparoscopic forceps. The fourth trocar is used for the introduction of instruments as well as the electrocatheter to be implanted in the stomach wall of the patient. The structure of the electrocatheter plays an important part in facilitating the specific operation for whichever of the patient's organs and/or viscera the surgeon aims to stimulate.

Each of the trocars used, of course, requires a separate tract through the skin and abdominal wall. To keep the abdomen inflated, valves are used with the trocars to provide a gas-tight seal. Introduction of a medical device, such as an electrocatheter or implantable electrode, into the abdomen generally requires the use of laparoscopic forceps to grasp the device. Such devices, which are generally inherently fragile in nature, could be damaged if grasped too firmly by the forceps. Thus, for example in the case of an electrocatheter having electrode leads, the interior conductor wires could be broken, rendering the device dysfunctional or completely useless.

It Would be desirable, therefore, to provide an improved implant device which can be easily and precisely positioned for attachment to the target tissue or organ and which can be controlled in place to provide the electrical path through the anode and cathode to provide improved electrostimulation and/or monitoring for the tissue of interest. It would also be desirable to provide an improved implant device with a plurality of micro-electrodes which allows variable electrical pathways such that improved electrical stimulation and/or monitoring of the target tissue or organ can be achieved. It would also be desirable to provide an improved implant device wherein the electrical path can be modified as needed to take into account shifting or movement of the implant device over time in order to maintain the desired electrostimulation and/or monitoring of the tissue of interest. The present invention provides such implant devices. The present implant devices allow precise placement of the electrode leads relative to the tissue to be treated. The present implant devices provide flexibility with regard to electrostimulation of the tissue to be treated. Moreover, the present implant devices provide flexibility to modify the electrical path through the electrodes to allow for precise electrostimulation of the tissue to be treated both at the time of implantation and at later times wherein the optimum location for electrostimulation may be changed due to movement of the implant device itself or due to the changing medical condition of the patient. Moreover, the present implant devices provide flexibility and accuracy by allowing directional sensing and/or directional stimulation of tissue (including for example, brain tissue). The present implant device would be especially useful, for example, for treatment of neurological conditions in the brain (as well as other neurological tissue such as spinal tissue). The present implant devices are also useful, for example, for electrostimulation and/or monitoring of tissue and/or organs of the gastrointestinal tract.

SUMMARY OF THE INVENTION

This invention relates to medical implant devices having a plurality of micro-electrodes which allow directional electrostimulation and/or directional monitoring of tissue, especially neurological tissue, in a mammal and especially in humans. The medical implant devices of this invention are designed and adapted for use in laparoscopic surgery and/or other surgical or microsurgical procedures. This medical implant device is especially adapted for precise and proper placement of the electrodes relative to the tissue to be treated. Additionally, the electrical pathway of the medical implant device, once properly placed adjacent to or within the tissue to be treated, can be modified without moving and/or adjusting the position of the medical implant device relative to the tissue to be treated.

For purposes of this invention, "micro-electrodes" or "discrete micro-electrodes" are electrodes formed within or along the outside circumference of the elongated body but which do not extend fully around the outside circumference. As shown in FIG. 4A, such a micro-electrode forms only a portion of the circumference as defined by angle $\alpha$. Generally, the angle $\alpha$ is less than about 90° and more preferably less than about 45°. Such micro-electrodes provide for directional electrostimulation and/or electrical monitoring.

This medical implant device employing multiple discrete micro-electrodes is especially adapted for electrostimulation and/or electrical monitoring of neuroglial or neuro-muscular tissue including, but not limited to, brain tissue (especially deep brain tissue located near or within the thalamus). Generally, the implant devices of this invention adapted for neuroglial or neuro-muscular tissue have an elongated body having a plurality of discrete micro-electrodes at the distal end which are electrically connected to an electric connection terminal at the proximal end for connection to a power source. In one preferred embodiment, the medical implant device adapted for neurological and neuro-muscular tissue is a pacemaker system having an implantable medical device with discrete micro-electrodes designed and adapted for electrostimulation and/or electrical monitoring of neurological and neuro-muscular tissue, including brain tissue, in a mammal.

Although especially adapted for use in electrostimulation or monitoring of neurological and neuro-muscular tissue, the micro-electrodes of this invention can be used for electrostimulation or monitoring of other tissue and/or organs such as, for example, endo-abdominal tissue or viscera. Thus, in another preferred embodiment, the elongated body is equipped with immobilizing or securing devices to secure it to the tissue or organ (e.g., endo-abdominal tissue or viscera) to be treated, a plurality of micro-electrodes that are electrically connected to an electric connection terminal for connection to a power source, a mechanism to penetrate the tissue or organ to be treated, and quick-release connecting devices to separate the penetration device from the elongated body. The implant devices of this invention having discrete micro-electrodes allow for modification of the electrical pathway through the tissue to be stimulated, treated, and/or monitored without moving or repositioning the implant device itself. Thus, the electrical pathway passing through a pulsing micro-electrode, the tissue, and the return micro-electrode can be adjusted as needed to obtain more optimal results without moving or repositioning the implant device itself. The improved medical implant devices of this invention allow more precisely controlled positioning of the electrode leads and, thus, the electrical pathway through the tissue to be stimulated, treated, and/or monitored.

This implant device can be easily inserted and properly placed in, or adjacent to, the tissue or viscera to be stimulated since the actual electrical pathway, including its directional aspect with respect to the tissue to be treated, can be modified in situ. This improved implant device includes a plurality of discrete micro-electrodes on a elongated implant body to provide directional sensing or pacing of target tissue. Preferably, the number of such discrete micro-electrodes is three or more, and more preferably, about 4 to about 20. Using a significant number of such micro-electrodes, the actual electrodes used (i.e., the selected pulsing micro-electrode and the selected return micro-electrode which, along with the tissue to be treated, form the electrical pathway) can be selected to provide optimal results. Additionally, different micro-electrodes can later be selected to form the electrical pathway so that time-dependent changes (e.g., movement of the implant device or changes in the tissue to be treated) can be accounted for without moving or repositioning the implant device. If desired, more than one electrical pathway (generally pulsed in sequence) can be used to provide electrostimulation. As shown in FIG. 2, the tissue to be treated can be electrostimulated using, for example, electrical pathways 5A and 5B in alternating or repeating sequences (i.e, 5A, 5B, 5A, 5B . . . ). Of course, additional electrical pathways or different sequencing patterns could be used if desired.

In one embodiment especially adapted for treatment of neuroglial or neuro-muscular tissue, the implant device is an elongated body with (1) a plurality of micro-electrodes at its distal end, (2) an electric connection terminal at the proximal end for connection to a power source, (3) a plurality of electrical conductors extending through the elongated body from the distal end to the proximal end so that any pair of the plurality of micro-electrodes can be electrically connected to the electric connection terminal to form an electrical pathway between the electric connection terminal, the pair of the plurality of the micro-electrodes, and the neuroglial or neuro-muscular tissue to be treated, and (4) a multiplexer or switching device such that the pair of the plurality of micro-electrodes can be selected to form the electrical pathway. In an especially preferred embodiment, the medical implant device is included in a pacemaker system designed and adapted for electrostimulation and/or electrical monitoring of neurological and neuro-muscular tissue, including brain tissue, in a human suffering from neurological tremors.

For use with other tissue, the implant device comprises an elongated body having (1) immobilizing or securing devices to secure it to the tissue or organ (e.g., endo-abdominal tissue or viscera) to be treated, (2) a plurality of micro-electrodes located on the elongated body, (3) an electric connection terminal at the proximal end for connection to a power source, (4) a plurality of electrical conductors extending through the elongated body from the plurality of micro-electrodes to the proximal end so that any pair of the plurality of micro-electrodes can be electrically connected to the electric connection terminal to form an electrical pathway between the electric connection terminal, the pair of the plurality of micro-electrodes, and the neuroglial tissue to be treated, (5) a multiplexer or switching device such that the pair of the plurality of micro-electrodes can be selected to form the electrical pathway, and (6) a mechanism, located at the terminal end of the elongated body, to penetrate the tissue or organ to be treated, and (7) quick-release connecting devices to separate the penetration device from the elongated body. This embodiment is especially adapted for electrostimulation and/or monitoring of tissue and internal organs within the endo-abdominal cavity of a mammal or, more preferably, humans. Examples of such endo-abdominal tissue and internal organs include, but are not limited to, the stomach, small intestine, large intestine, urinary bladder, gall bladder, muscles of the abdominal cavity, and tissue, muscles, and/or organs of the thoracic cavity (including, but not limited to, the cervical, thoracic, and abdominal portions of the esophagus and the pharyngeal musculature in the neck), and the like.

The present invention also provides an improved medical device having a plurality of micro-electrodes and which can be positioned easily and precisely such that at least some of the micro-electrodes are in good electrical contact with the tissue to be treated. The present invention also provides an improved medical device having a plurality of micro-electrodes such that the electrodes can provide directional electrostimulation and/or monitoring.

The present invention also provides an implant device especially adapted for treatment of neuroglial or neuro-muscular tissue, the implant device comprising (1) an elongated body with a distal end and a proximal end; (2) a plurality of micro-electrodes at the distal end; (3) an electric connection terminal at the proximal end for connection to a power source; (4) a plurality of electrical conductors extending through the elongated body from the distal end to the proximal end, wherein each electrical conductor is attached to a single micro-electrode at the distal end, whereby any selected pair of the plurality of micro-electrodes can be electrically connected to the electric connection terminal to form an electrical pathway between the electric connection terminal, the selected pair of the plurality of micro-electrodes, and the neuroglial or neuro-muscular tissue to be treated; and (5) a multiplexer or switching device such that the selected pair of the plurality of micro-electrodes can be used to form the electrical pathway.

The present invention also provides an implant device for electrostimulation or electrical monitoring of tissue to be treated within a body cavity, said implant device comprising (1) an elongated body having a distal end and a proximal end; (2) a penetration mechanism at the distal end to penetrate the tissue to be treated; (3) a quick release connecting mechanism adjacent to the penetration mechanism, wherein the quick release connecting mechanism is effective to separate the penetration device from the elongated body once the implant device is properly positioned in the body cavity; (4) a first immobilizing mechanism and a second immobilizing mechanism adjacent and proximal to the quick release connecting mechanism to secure the implant device to the tissue to be treated wherein the first and second immobilizing mechanisms are spaced apart along the elongated body a distance sufficient to span the tissue such that the first immobilizing mechanism is located between the quick release connecting mechanism and the second immobilizing mechanism; (5) a plurality of micro-electrodes located between the first and second immobilizing mechanisms; (6) an electrical connection terminal at the proximal end for connection to a power source; (7) a plurality of electrical conductors extending through the elongated body from the plurality of micro-electrodes to the proximal end, wherein each electrical conductor is attached to a single micro-electrode, whereby any selected pair of the plurality of micro-electrodes can be electrically connected to the electric connection terminal to form an electrical pathway between the electric connection terminal, the selected pair of the plurality of micro-electrodes, and the tissue to be treated; and (8) a multiplexer or switching device such that the selected pair of the plurality of micro-electrodes can be used to form the electrical pathway.

The present invention also provides a method for electrostimulation of neuroglial or neuro-muscular tissue, said method comprising (a) positioning an implant device having a distal end and a proximal end such that the distal end can provide electrical stimulation of the neuroglial or neuro-muscular tissue, wherein the distal end of the implant device has a plurality of micro-electrodes and the proximal end of the implant device has an electrical connection terminal for connection to an electrical pulse generator, and wherein various pairs of the micro-electrodes can be electrically connected to the electrical connection terminal, (b) positioning the distal end of the implant device sufficiently close to the neuroglial or neuro-muscular tissue to be electrostimulated, (c) attaching the electrical pulse generator to the electrical connection terminal of the implant device, (d) delivering electrical impulses to the implant device whereby various pairs of the plurality of micro-electrodes can be tested for electrostimulation of the neuroglial or neuro-muscular tissue, and (e) selecting a pulsing micro-electrode and a receiving micro-electrode from the various pairs of the plurality of micro-electrodes tested in step (d) to provide the good electrostimulation of the neuroglial or neuro-muscular tissue.

The present invention also provides a method for electrostimulation of gastrointestinal tissue, said method comprising (a) inserting an implant device though a trocar into the endo-abdominal cavity, wherein the implant device has a plurality of micro-electrodes and an electrical connection terminal for connection to an electrical pulse generator, wherein various pairs of the micro-electrodes can be electrically connected to the electrical connection terminal, (b) positioning the plurality of micro-electrodes within an area of the gastrointestinal track to provide electrical stimulation to the gastrointestinal tissue to be electrostimulated, (c) immobilizing the implant device so as to maintain good electrical stimulation of the gastrointestinal tissue to be electrostimulated during a treatment regime, (d) attaching the electrical pulse generator to the electrical connection terminal of the implant device, (e) delivering electrical impulses to the implant device whereby various pairs of the plurality of micro-electrodes can be tested for electrical stimulation of the gastrointestinal tissue to be electrostimulated, (f) selecting a pulsing micro-electrode and a receiving micro-electrode from the various pairs of the plurality of micro-electrodes tested in step (e) to provide the good electrically stimulation of the of the gastrointestinal tissue to be electrostimulated, and (g) using the selected pulsing micro-electrode and received micro-electrode to electrostimulate the gastrointestinal tissue. Preferably the gastrointestinal tissue subjected to electrostimulation is associated with the Auerbach plexus and/or the Meissner plexus.

The present invention also provides a method for clinically effective electrostimulation of gastrointestinal tissue, said method comprising (a) implanting an implant device in the endo-abdominal cavity, wherein the implant device has a plurality of micro-electrodes and an electrical connection terminal for connection to an electrical pulse generator, wherein various pairs of the micro-electrodes can be electrically connected to the electrical connection terminal, (b) positioning the plurality of micro-electrodes within an area of gastrointestinal track to provide electrical stimulation to the gastrointestinal tissue to be electrostimulated, (c) immobilizing the implant device so as to maintain good electrical stimulation of the gastrointestinal tissue to be electrostimulated during a treatment regime, (d) attaching the electrical pulse generator to the electrical connection terminal of the implant device, (e) delivering electrical impulses to the implant device whereby various pairs of the plurality of micro-electrodes can be tested, (f) measuring the impedance between the various pairs of the plurality of micro-electrodes, (g) selecting a pulsing micro-electrode and a receiving micro-electrode from the various pairs of the plurality of micro-electrodes tested in step (e), wherein the selected pulsing micro-electrode and the selected receiving micro-electrode pair has the lowest, or close to the lowest, impedance measured in step (f), and (h) providing electrostimulation of the gastrointestinal tissue using the selected pulsing micro-electrode and the selected receiving micro-electrode pair. In an especially preferred method, the impedance is automatically measured between the various pairs of the plurality of micro-electrodes periodically (e.g., once an hour, once every four hours, once every twelve hours, once a day, or the like) to identify and select the micro-electrode and the receiving micro-electrode pair having the lowest impedance to provide good electrostimulation to the tissue to be stimulated over time. Should the implant device shift within the penetration tunnel, this method would allow a new and more effective micro-electrode pair to be selected at the next periodic measuring time or interval.

The present invention also provides a method for clinically effective electrostimulation of neuroglial or neuro-muscular tissue, said method comprising (a) positioning an implant device having a distal end and a proximal end such that the distal end can provide electrical stimulation of the neuroglial or neuro-muscular tissue, wherein the distal end of the implant device has a plurality of micro-electrodes and the proximal end of the implant device has an electrical connection terminal for connection to an electrical pulse generator, and wherein various pairs of the micro-electrodes can be electrically connected to the electrical connection terminal, (b) positioning the distal end of the implant device sufficiently close to the neuroglial or neuro-muscular tissue to be electrostimulated, (c) attaching the electrical pulse generator to the electrical connection terminal of the implant device, (d) delivering electrical impulses to the implant device whereby various pairs of the plurality of micro-electrodes can be tested for electrostimulation of the neuroglial or neuro-muscular tissue, and (e) measuring the impedance between the various pairs of the plurality of micro-electrodes;

(f) selecting a pulsing micro-electrode and a receiving micro-electrode from the various pairs of the plurality of micro-electrodes tested in step (d), wherein the selected pulsing micro-electrode and the selected receiving micro-electrode pair has the lowest, or close to the lowest, impedance measured in step (e); and (g) providing electrostimulation of the neuroglial or neuro-muscular tissue using the selected pulsing micro-electrode and the selected receiving micro-electrode pair. In an especially preferred method, the impedance is automatically measured between the various pairs of the plurality of micro-electrodes periodically (e.g., once an hour, once every four hours, once every twelve hours, once a day, or the like) to identify and select the micro-electrode and the receiving micro-electrode pair having the lowest impedance to provide good electrostimulation to the tissue to be stimulated over time. Should the implant device shift within the penetration tunnel, this method would allow a new and more effective micro-electrode pair to be selected at the next periodic measuring time or interval.

These and other features and advantages of the present invention will become apparent to those skilled in the art upon a reading of the following detailed description when taken in conjunction with the drawings wherein there is shown and described preferred embodiments of the invention.

BRIEF DESCRIPTION OF THE DRAWINGS

FIG. 1 is a schematic side view of one embodiment of the implant device according to this invention which is especially designed for electrostimulation and/or monitoring of neuroglial or neuro-muscular tissue.

FIG. 2 illustrates the distal end of the implant device of FIG. 1 positioned adjacent to neuroglial or neuro-muscular tissue to be stimulated.

FIGS. 3A and 3B are schematic side views of the distal end of the implant device of FIG. 1 having micro-electrodes of different arrangements and shapes.

FIG. 4 provides cross-sectional views of elongated bodies having micro-electrodes. Panel A has two micro-electrodes; Panel B has four micro-electrodes; and Panel C has eight micro-electrodes. The arrangement of Panel B corresponds to the micro-electrodes of FIG. 3A along sectional line 14. These cross-sectional views can be associated with the implant devices of either FIG. 1 or FIG. 5.

FIG. 5A shows the penetration device attached to the elongated body whereas

FIG. 6A illustrates placement of the implant device where the length of penetration tunnel is approximately equal to the distance between the two immobilizing units. In FIG. 6B, both the distal and proximal portions of the implant device extends outside the penetration tunnel; in FIG. 6C, the distal end of the implant device extends outside the penetration tunnel. The implant devices shown in FIGS. 6A and 6B are as illustrated in FIGS. 5A and 5B; the implant device shown in FIG. 6C is as illustrated in FIG. 5C. Individual micro-electrodes are labeled A through J.

DETAILED DESCRIPTION OF THE PREFERRED EMBODIMENTS

Figure 5A:
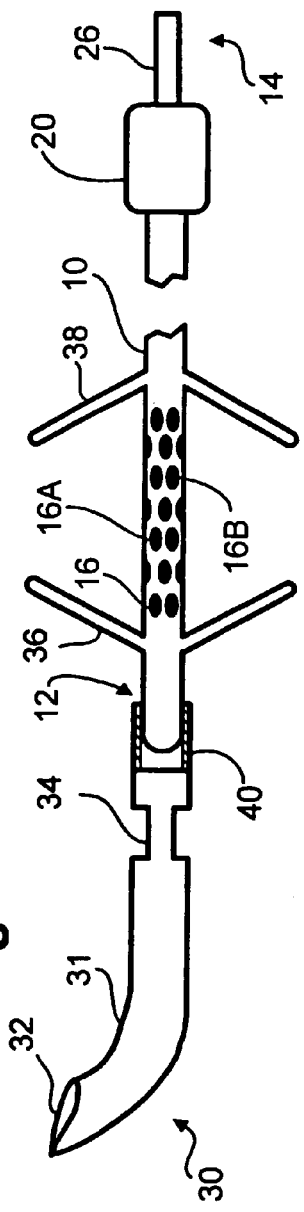
FIG. 5A illustrates other embodiments of the implant device according to this invention which is especially designed for electrostimulation and/or monitoring of gastrointestinal tissue.

The present invention provides implant devices specifically for in situ electrostimulation and/or electrical monitoring in mammals and, more particularly, in humans. The implant devices of this invention employ a plurality of (and preferably at least 3) micro-electrodes, wherein the micro-pulsing and receiving micro-electrodes can be selected once the implant is in place. By this delayed selection of the pulsing and receiving micro-electrodes, good electrical contact between the pulsing and receiving micro-electrodes and the tissue to be treated can more easily be obtained. Moreover, should the physical location of implant device change slightly during use or the condition of the tissue being treated change, the selection of the appropriate pulsing and receiving micro-electrodes can be repeated to account for such changes and help insure continuing good electrical contact. Although the elongated body of the implant devices of this invention preferably are circular in cross-section (see FIG. 4), other cross-sectional shapes or forms can be used if desired.

The implant device has an elongated body equipped with a plurality of micro-electrodes such that any pair ($N_i$, $N_j$) of such micro-electrodes can be used for electrostimulation and/or monitoring. In most cases, it is expected that the electrical pathway defined by $N_i$ and $N_j$ will be independent of direction of the electrical pathway (i.e., pair $N_i$ and $N_j$ will be equivalent to pair $N_j$ and $N_i$). Thus, for an implant having n micro-electrodes, the number of possible pairs or combinations is $n!/(2(n-2)!)$. Thus, for example, when n is 5 (see FIG. 1), the number of possible pairs is 10; when n is 20 (see FIGS. 2A and 2B), the number of possible pairs is 190; when n is 28 (see FIGS. 5A and 5B), the number of possible pairs is 378. Generally, n is preferably greater than 3 and, more preferably between 4 and 20. In practice and especially when n is large, it may not be necessary to evaluate each possible pair. Rather, a reasonable subset of such possible pairs can be evaluated until a suitable electrostimulation or monitoring electrical pathway or desired clinical objective is obtained. Out of such a reasonable subset, a suitable electrical pathway (or pathways) can be selected or obtained so long as at least one of the pathways is clinical suitable.

Generally, a reasonable subset will be less than 50 such pairs and, more preferably, less than about 20 such pairs. In some cases, however, more pairs may need to be evaluated in order to find suitable pairs. Such searching for suitable pairs is preferably carried out using computer techniques wherein various pairs can be evaluated for good electrical contact and/or clinical effect.

FIG. 1 illustrates an implant device specifically designed for electrostimulation and/or monitoring of neuroglial or neuro-muscular tissue; this implant device can, however, be used with other tissue types if desired. The implant device consists of an elongated body 10 having a distal end 12 and a proximal end 14. Located at the distal end 12 are a plurality of micro-electrodes 16. Each of the micro-electrodes 16 are electrically connected to a multiplexer or switching device 20 via electrical conductors 11 passing through the lumen of the elongated body 10. The multiplexer or switching device 20, preferably contained on a computer chip or other programable device, can be used to select or evaluate various combinations of micro-electrodes 16 to allow selection of the appropriate pulsing micro-electrode 16A and receiving micro-electrode 16B. Pulsing electrical line 22 and receiving electrical line 24 run from the multiplexer or switching device 20 to the electrical connection terminal 26. The electrical connection terminal 26 can be attached to electrical pulse generator or pacemaker 28. Rather than being located along the elongated body, the multiplexer or switching device 20 can be (1) located at or near the proximal end 14 of the elongated body, (2) incorporated into the electrical connection terminal 26, or (3) incorporated into the electrical pulse generator or pacemaker 28.

As shown in FIG. 3, the micro-electrodes 16 of the implant device shown in FIG. 1 are located at the distal end 12 of the elongated body 10. FIGS. 3A and 3B illustrates differing shapes for the micro-electrodes; of course other shapes for the micro-electrodes can be used. Assuming the pattern of the micro-electrodes 16 is repeated on the opposite or reverse surface of the elongated body (i.e., the arrangements of micro-electrodes through line 14 would provide one additional micro-electrode on the opposite side and the arrangement through line 15 would provide two additional micro-electrodes on the opposite side), the implant devices shown in FIGS. 3A and 3B would have 20 micro-electrodes. Thus, the micro-electrodes can be combined in 190 pairs and can, therefore, potentially provide 190 different electrical pathways through the tissue to be treated.

FIG. 4 provides a cross-sectional views of various arrangement of micro-electrodes 16 along the elongated body 10. The micro-electrodes 16 may extend from the elongated body 10 (FIGS. 4A and 4B) or may be co-planar with the elongated body 10 (FIG. 4B). As shown in FIG. 4, the number and shapes of micro-electrodes 16 can be varied. As noted above, other cross-sectional shapes or forms (i.e., oval, rectangular, and the like) can be used if desired.

FIG. 2 illustrates the placement of the implant device of FIG. 1 adjacent to or within a tunnel or natural fissure 8 of neuroglial or neuro-muscular tissue 6 (e.g., brain tissue) to be treated. The distal end 12 is placed adjacent to the tissue to be treated so that at least some of the plurality of micro-electrodes are placed in electrical contact with the neuroglial or neuro-muscular tissue 6 around the tunnel or natural fissure 8. Micro-electrodes 16A and 16B are properly positioned (as are a number of other micro-electrode pairs) to provide electrical stimulation and/or monitoring of the neuroglial tissue 6. An electrical pathway 5A can be formed through micro-electrode 16A, the neuroglial or neuro-muscular tissue 6 to be treated, and micro-electrode 16B. Of course, other electrical pathways could be utilized depending on the selection of the micro-electrodes 16A and 16B. Also as shown in FIG. 2, micro-electrode 16C (as well as other micro-electrodes) would not be suitable since they are located outside the tunnel or natural fissure 8 and do not electrically contact the tissue to be treated.

As those skilled in the art will realize, contact of a given micro-electrode with the tissue of be treated is a necessary, but not sufficient, condition to be considered in the selection of the pulsing and receiving micro-electrodes. Thus, for example, although a given micro-electrode may be in contact with the desired tissue to be treated, the electrical pathway 5 obtained with that micro-electrode may not provide the desired clinical effect. Even when a particular micro-electrode both provides contact and the desired clinical effect, there may still be other electrical pathways which provide even better clinical results. In other words, electrical pathways 5A and 5B (as well as may others) may be established with the tissue to be treated, but some electric pathways may provide better clinical results. Thus, it may be desirable to evaluate other electrical pathways even after a satisfactory (but not necessarily optimal) pathway is identified. Moreover, different electrical pathways may provide better clinical results at different times. For example, the optimum electrical pathway may change with time because of changes due to movement of the micro-electrodes 16 and/or the tissue 6 relative to each other or because of clinical changes in the condition of the tissue to be treated.

Figure 5B:
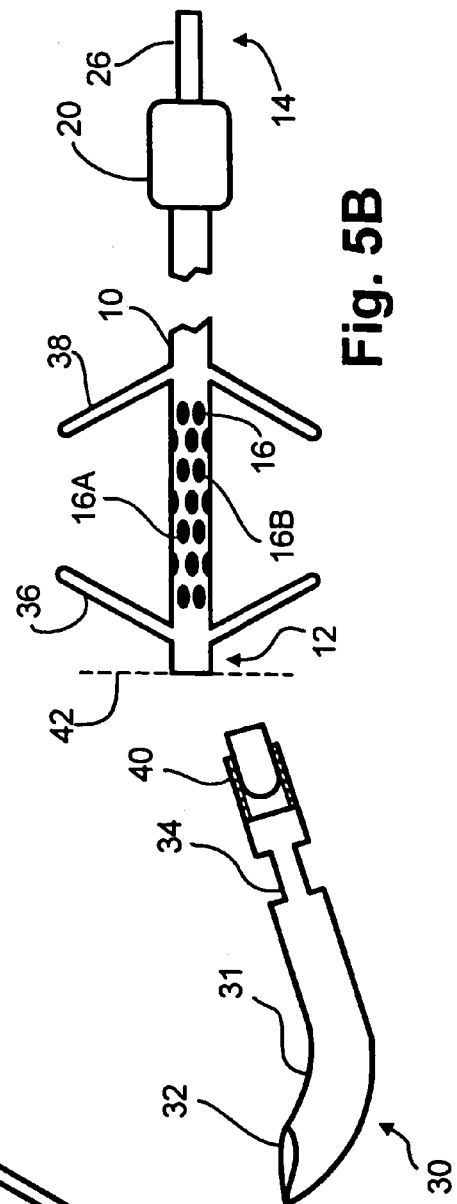
FIG. 5B shows the penetration device removed.
Figure 5C:
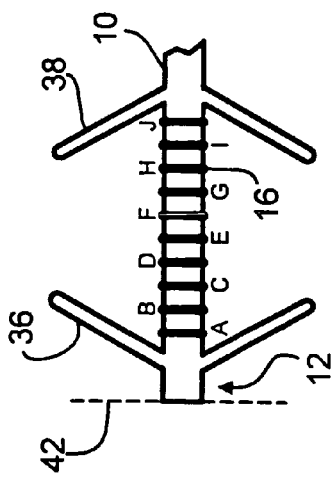
FIG. 5C illustrates a portion of the implant device having micro-electrodes which encircle the elongated body between the immobilizing units.
Figure 6A:
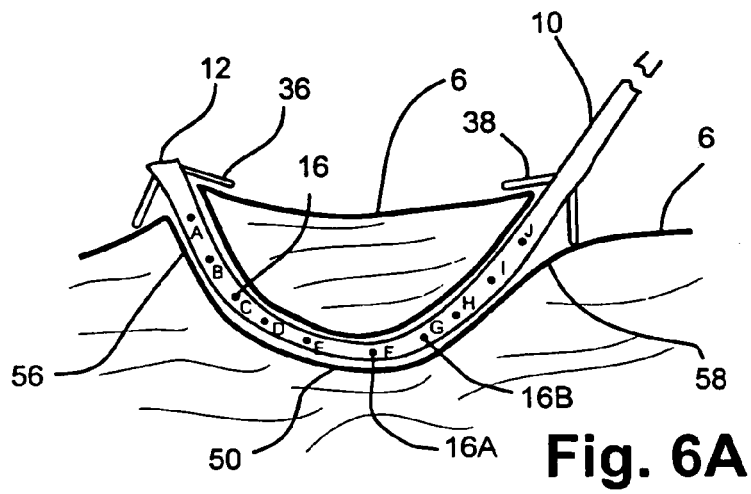
FIG. 6A illustrates the implant device of FIG. 5 positioned within a penetration tunnel after removal of the penetration device.
Figure 6B:
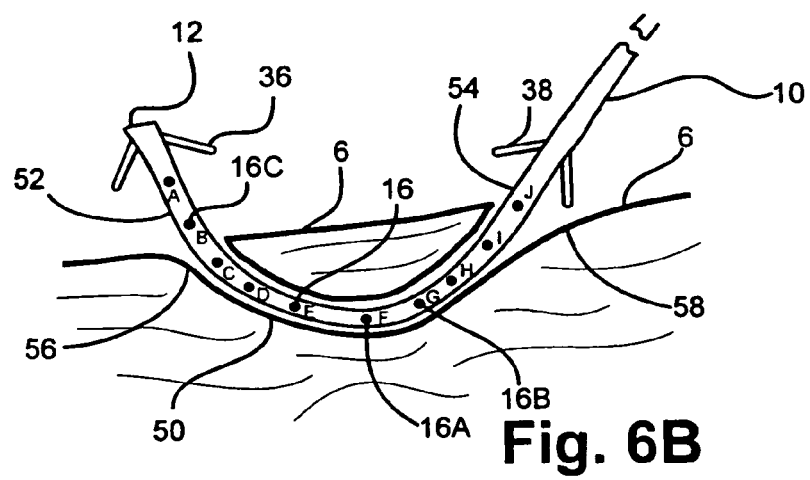
FIGS. 6B and 6C illustrate placement of the implant device where the length of penetration tunnel is significantly less than the distance between the two immobilizing units.
Figure 6C:
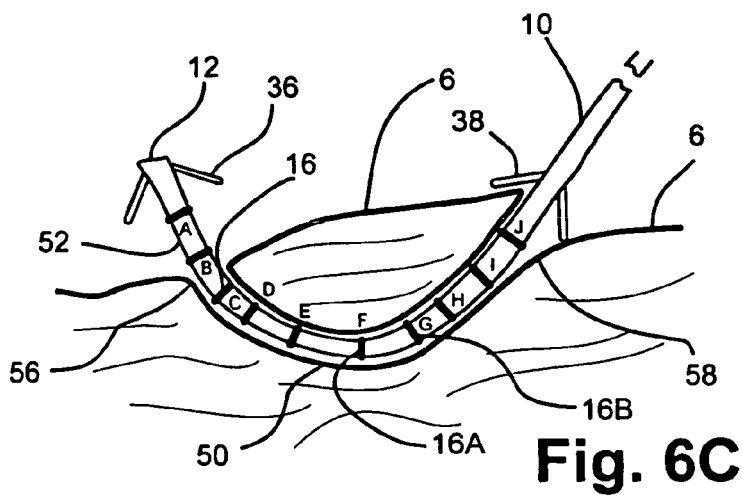

FIG. 5 illustrates an implant device with micro-electrodes 16 especially adapted for use in electrostimulation and/or monitoring of other tissue such as, for example, gastrointestinal tissue. In this implant device, the micro-electrodes 16 are located along the elongated body 10 and between the immobilizing mechanisms 36 and 38 (used to secure it to the gastrointestinal wall) such that the micro-electrodes 16 are electrically connected to an electrical connection terminal 26 for connection to a power source (not shown) via multiplexer or switching mechanism 20. The implant device also has a mechanism 30 to penetrate the gastrointestinal wall and a quick release connecting mechanism 40 to separate the penetration device 30 from the elongated body once the device is properly situated. FIG. 5A illustrates the implant device with the penetration mechanism 30 attached to the distal end 12; FIG. 5B illustrates the implant device once the penetration device 30 is detached, along line 42, from the elongated body. FIG. 5C illustrates a portion of the elongated body 10 between the immobilizing units 36 and 38 wherein the micro-electrodes 16 surround or encircle the elongated body 10. FIGS. 6A, 6B, and 6C illustrate placement of the implant device within the penetration tunnel 50 formed in the tissue to be treated using the penetration device 30 (which has been detached).

Figure 7A:
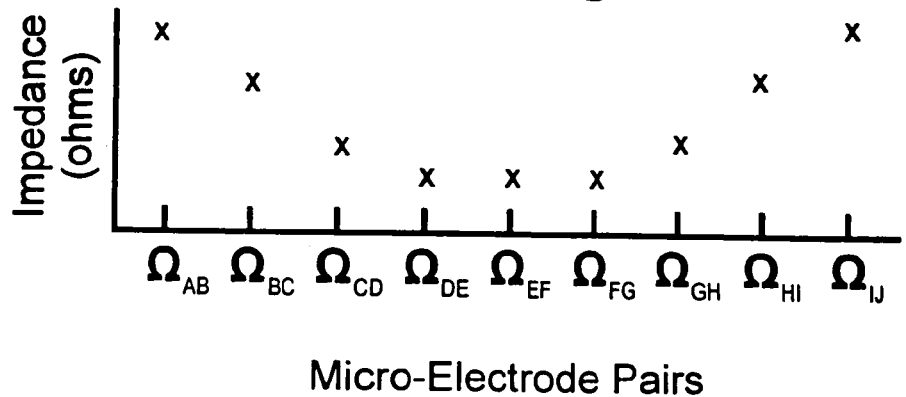
FIG. 7A provides graphs showing variations of impedance between adjacent micro-electrodes as labeled in FIG. 7A. Panel A corresponds to FIG. 6A.
Figure 7B:
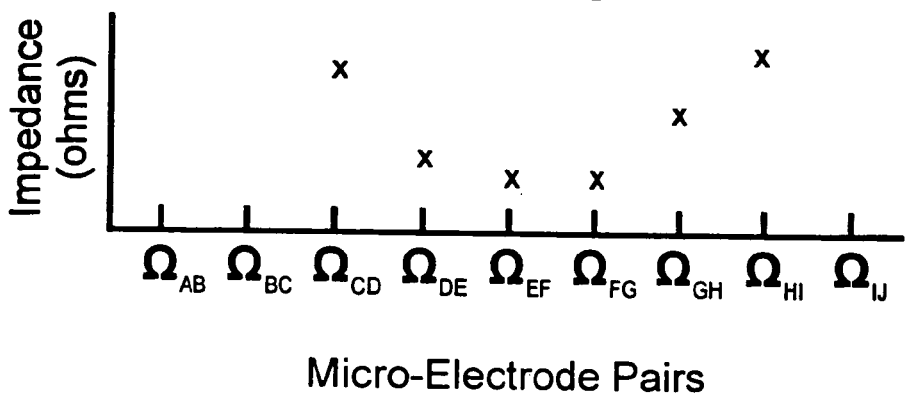
FIG. 7B corresponds to FIG. 6B.
Figure 7C:
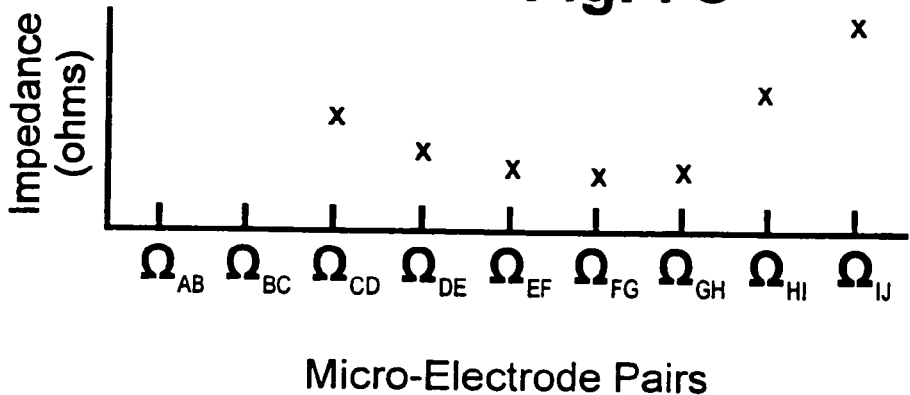
FIG. 7C corresponds to FIG. 6C.

In a preferred method, the impedance is measured between various micro-electrodes 16 at the programmed amplitude of stimulation in order to determine the optimum micro-electrodes for use as the pulsing 16A and receiving 16B micro-electrodes. Preferably, the impedance is measured between adjacent micro-electrodes (e.g., A–B, B–C, C–D, . . . H–I, I–J in FIGS. 6A, 6B, and 6C) or closely spaced micro-electrodes. Generally, the pair of micro-electrodes buried deepest within the tissue to be stimulated will have the lowest impedance and will, therefore, provide the optimum pulsing 16A and receiving 16B micro-electrode pair. FIGS. 7A, 7B, and 7C (i.e., plots of impedance measured between adjacent pairs of micro-electrodes as implanted in FIGS. 6A, 6B, and 6C, respectively) illustrate the use of this method to select the optimum micro-electrode pair. In FIG. 7, $\Omega_{AB}$ is the impedance measured between micro-electrodes A and B. FIG. 7A (corresponding to the implant device in FIG. 6A) indicates that all pairs of micro-electrodes are within the penetration tunnel; the low impedance between pairs DE, EF, and FG, however, suggests that any of these pairs could provide optimum results. FIG. 7B (corresponding to the implant device in FIG. 6B) indicates that pairs of micro-electrodes AB, BC, and IJ would not be acceptable; the low impedance between pairs EF and FG, however, suggests that either of these pairs could provide optimum results. FIG. 7C (corresponding to the implant device in FIG. 6C) indicates that pairs of micro-electrodes AB and BC would not be acceptable; the low impedance between pairs EF, FG, and GH however, suggests that any of these pairs could provide optimum results. Once an optimum pair of micro-electrodes has been selected, groups of adjacent micro-electrodes could be combined or coupled to provide greater electrode surface area and even lower impedance. For example, in FIGS. 6A and 7A, micro-electrode pair EF could be selected at the optimum pair. Micro-electrodes C and D could then be grouped with micro-eclectrode E to provide a single electrode (i.e., CDE) of one polarity; likewise, micro-electrodes G and H could be grouped with micro-electrode F to provide a single electrode (i.e., FGH) of opposite polarity. The combined electrodes CDE and FGH could be used as the pulsing 16A and receiving 16B micro-electrode pair, respectively.

This method for selecting the optimum pulsing 16A and receiving 16B micro-electrode pair can be implemented once the implant device has been positioned within the tissue to be stimulated and can be repeated as desired. Alternatively, the implant device can be equipped with a computer chip or other circuitry (incorporated, for example, in the electrical pulse generator or pacemaker 28) to periodically measure the impedance between the various micro-electrodes pairs and, if appropriate, modify the pulsing 16A and receiving 16B micro-electrode pair selected. Such a method would allow the implant device to be repeatedly optimized for electrostimulation even if the implant device shifts within the penetration tunnel. The impedance could be measured, for example, once an hour, once every four hours, once every twelve hours, once a day, or the like. Thus, should the implant device shift within the penetration tunnel, this method would allow a new and more effective micro-electrode pair to be selected at the next periodic measuring time or interval. If desired, the data resulting from this periodic measurement of impedance could be stored for later downloading and analysis. Changes in substrate conditions might, for example, be reflected in increases or decreases in the impedance value (i.e., along the vertical axis of FIG. 7) for a given set of micro-electrodes. Shifts in the impendence profile (i.e., along the horizontal axis of FIG. 7) would suggest shifting within the penetration tunnel and even imminent dislodgement. Such data might be helpful in determining if, and when, to remove or otherwise modify the implanted device.

The implant device specifically for electrostimulation and/or electrical monitoring of the endo-abdominal viscera is shown in FIG. 5 and includes an elongated body 10 of the electrocatheter equipped with an immobilizing or securing mechanisms consisting of distal tines 36 and proximal tines 38 to lock the electrocatheter in place and to secure it to the visceral wall (not shown). The micro-electrodes 16 are electrically and individually connected to a multiplexer or switching device 20 such that any two of the micro-electrodes 16 can be connected in an electrical pathway. From the multiplexer or switching device 20, each of the possible pairs of micro-electrodes (e.g., 16A and 16B) can be connected to an electrical connection terminal pin 26 at the proximal end 1. The electrical connection terminal pin 26 is connected to a power source or pacemaker (not shown). The power source or pascemaker may be, for example, an electric pulsator with an operating frequency of a preset number of pulses per minute. Throughout this discussion, the distal side or end 12 of the implant or elements is considered to be in the direction of the penetration mechanism 30 and the proximal side or end 14 is considered to be in the direction of the electrical connection terminal pin 26 in FIGS. 5A, 5B, and 5C.

More specifically, the implant device includes penetration mechanism 30 capable of penetrating the gastrointestinal wall and forming a penetration tunnel in the tissue to be treated and mechanism 40 for connection and quick-release of penetration mechanism 30 to the elongated body 10 of the electrocatheter. In particular, penetration mechanism 30 includes a solid tunneling device or stylet 31 with a cutting part 32 at the distal end. Preferably, the penetration mechanism 30 includes a flattened portion or slot 34 which can be used for grasping with laparoscopic forceps. Located at the opposite or proximal end of the penetration mechanism 30 is attachment and/or quick release mechanism 40 through which attachment to the elongated body 10 is made.

The outer insulating cover on elongated body 10 and connecting element 40 are preferably formed from silicone (preferably medical grade) or other bio-compatible material having similar characteristics. The length of the connecting element 40 is adjusted to permit angling and flexibility without harming the electrical components located within the elongated body. In addition, the connecting element 40 preferably is radiopaque. Advantageously, during video-laparoscopic surgery, in order to separate the stylet 31 from the elongated body 10 of the electrocatheter, it is sufficient to cut it with scissors or other devices (not shown) in order to be able to remove the stylet from the abdominal cavity.

As shown in FIGS. 5A, 5B, and 5C, the immobilizing mechanisms include a first or distal set of projections, wings, or tines 36 and a second or proximal set of projections, wings, or tines 38. Preferably, the tines 36 and 38 are also made of silicone, but are not radiopaque. The distal tines 36 and proximal tines 38 are generally spread apart and in opposite directions from each other and are designed to maintain the micro-electrodes 16 of the implant device within the penetration tunnel 50 (see FIGS. 6A, 6B, and 6C) so that at least some of the micro-electrodes are maintained in electrical contact with the tissue to be electrostimulated and/or monitored. Generally, both the distal and proximal tines 36 and 38 are each at least two in number; preferably each set of tines are three to five in number. Preferably, the distal tines 36 and the proximal tines 38 have diameters of about 1 mm and lengths of about 3 mm. As those skilled in the art will realize, both the distal and proximal sets of tines may be of different numbers, sizes, and shapes so long as they serve their intended purpose of "locking" the implant to the tissue or viscera to be electrostimulated and/or monitored. The tines are flexible and are preferably formed from silicone (preferably medical grade) or other bio-compatible materials in order to minimize damage or stress to the tissue as the implant device is positioned and, after completion of treatment, removed.

In operation, the proximal tines 38 do not penetrate the thickness of the gastrointestinal wall or other tissue to be stimulated. Rather, they work with the distal pair to prevent the electrocatheter from being dislodged after insertion. In effect, the two sets of tines 36 and 38 allow the electrocatheter to be "locked" in place relative to the tissue to be stimulated without the need for any suturing to anchor the electrocatheter. Of course, the distance between distal and proximal immobilizing mechanisms will be related to the thickness of the tissue intended to be stimulated. As shown in FIGS. 6A, 6B, and 6C (wherein the penetration mechanism 30 has been removed, thereby leaving distal end 12 of the implant device extending from the penetration tunnel 50), using a plurality of micro-electrodes 16 makes the exact placement of the implant device within the penetration tunnel 50 less critical. FIG. 6A illustrates the preferred placement of the implant within the penetration tunnel 50; the length of the penetration tunnel 50 (i.e., the distance between the distal end 56 and the proximal end 58 of the penetration tunnel) is approximately equal to the distance between the distal 36 and proximal 38 immobilizing mechanisms. In FIG. 6A, almost all of the micro-electrodes could be used as the pulsing 16A or receiving 16B micro-electrodes since most of the micro-electrodes contact the tissue to be treated. The micro-electrodes 16A and 16B can be selected to provide the desired clinical effect.

As those skilled in the art will realize, placement of the implant device will often not provide the optimal placement as illustrated in FIG. 6A. The use of a plurality of micro-electrodes allows the implant device to be used even if the placement within the penetration tunnel 50 is not optimal or even close to optimal. Suboptimal placements are shown in FIGS. 6B and 6C. In FIG. 6B, neither the distal 36 nor proximal 38 immobilizing devices are in close contact with the distal end 56 or proximal end 58, respectively, of the penetration tunnel 50; in FIG. 6C, the distal immobilizing device 36 is not in close contact with the distal end 56 of the penetration tunnel 50. In fact, significant portions 52 (FIGS. 6B and 6C) and 54 (FIG. 6B) of the implant device extend outside the penetration tunnel 50. Of course, micro-electrodes (such as, for example, 16C) which are not within the penetration tunnel 50 would not be suitable for forming the electrical pathway. However, even with suboptimal placement, some of the micro-electrodes (such as, for example, 16A and 16B) will remain within the penetration tunnel 50 and, thus, provide suitable pulsing and receiving micro-electrodes since they are in electrical contact with the tissue to be treated. Moreover, from the subset of suitable pulsing and receiving micro-electrodes (i.e., having good electrical contact with the tissue), preferred pulsing and receiving micro-electrodes can be selected using clinical effect or result as the selection criteria.

As those skilled in the art will understand, the micro-electrodes can be used with a wide variety of implant devices or electrocatheters. Moreover, the immobilizing mechanisms can include, for example, tines, clamps, sutures, a flexible attachment member which can be folded back on the elongated body and attached to the elongated body thereby forming a closed loop around the tissue to be treated, and other locking devices. By "looping" around the tissue of interest, the attachment member and the elongated body are securely attached to the tissue and will resist displacement even in cases where the tissue is subject to vigorous peristaltic movement within the body (e.g., digestive organs). Other electrocatheters and/or immobilizing mechanisms are described in greater detail in U.S. Pat. No. 5,423,872 (Jun. 13, 1995); U.S. patent application Ser. No. 09/122,832 (filed Jul. 27, 1998), Ser. No. 09/358,955 (filed Jul. 22, 1999), Ser. No. 09/424,324 (filed Nov. 19, 1999), and Ser. No. 09/482,369 (filed Jan. 13, 2000); Patent Cooperation Treaty Application No. 98US98/10402 (filed May 21, 1998); and U.S. Provisional Application Ser. No. 60/151,459 (filed Aug. 30, 1999), all of which are hereby incorporated by reference in their entireties. Any of these earlier described implant devices can be easily modified to include the micro-electrodes of the present invention.

The implant devices of the present invention as shown in FIGS. 5 and 6 are especially adapted to provide electrical stimulation to the stomach for treating obesity and/or syndromes related to motor disorders of the stomach as described in U.S. Pat. No. 5,423,872 (issued Jun. 13, 1995). The stomach generally has three layers of smooth muscle—oblique, circular, and longitudinal muscle layers. The myenteric plexus (or Auerbach plexus) is generally located intermediate to the circular and longitudinal muscle layers while the submucous plexus (or Meissner plexus) is generally located intermediate to the oblique and circular muscle layers. It is generally preferred that the present implant device, when used to stimulate the stomach, is located such that Auerbach plexus, and more preferably both the Auerbach plexus and the Meissner plexus, are stimulated. Thus, in one embodiment, it is preferred that the penetration tunnel is formed within the stomach wall so as to allow for stimulation of the Auerbach plexus and the Meissner plexus. By situating the penetration tunnel through or adjacent to these nerve complexes (and thus the micro-electrodes once the implant has been positioned within the penetration tunnel), more effective direct stimulation of the nerves (as well as stimulation of the smooth muscle) can be effected. Alternatively, the Auerbach plexus and the Meissner plexus can be stimulated by placing the implant of this invention or other electrostimulation implants adjacent to the Auerbach plexus and the Meissner plexus so as to provide electrostimulation of the Auerbach plexus and the Meissner plexus; in such cases, a penetration tunnel would, of course, not be required.

It has been proven in practice that the implant device according to the invention is particularly useful as stated above. The invention so described may be subject to numerous modifications and variations, all of which fall within the scope of the inventive concept; furthermore, all the details may be replaced by technically equivalent elements. In practice, the materials used, as well as the dimensions, may be varied according to need and the state of the art.

Although the implant device of FIGS. 1 and 2 has been mainly described relative to its use with neuroglial or neuro-muscular tissue, it can be used with other tissue if desired. Likewise, although the implant device of FIGS. 5 and 6 has been mainly described relative to its use in the gastrointestinal tube, it is primarily intended to be used in the endo-abdominal cavity including all viscera therein; such viscera include, but are limited to, tissues associated with the stomach, large and small intestines, gall bladder, urinary tract, bladder, muscles, and the like. Moreover, although this implant device has been described in the context of use within the endo-abdominal cavity, it can, of course, be used in other portions of the body with appropriate modifications.

What is claimed is:

1. An implant device adapted for treatment of neuroglial or neuro-muscular tissue, said implant device comprising (1) an elongated body with a distal end and a proximal end; (2) a plurality of micro-electrodes at the distal end; (3) an electric connection terminal at the proximal end for connection to a power source; (4) a plurality of electrical conductors extending through the elongated body from the distal end to the proximal end, wherein each electrical conductor is attached to a single micro-electrode at the distal end, whereby any selected pair of the plurality of micro-electrodes can be electrically connected to the electric connection terminal to form an electrical pathway between the electric connection terminal, the selected pair of the plurality of micro-electrodes, and the neuroglial or neuro-muscular tissue to be treated; and (5) a multiplexer or switching device to measure impedance between the selected pair of the plurality of micro-electrodes in order to determine a satisfactory pair of the plurality of micro-electrodes to form the electrical pathway.

2. The implant device as in claim 1, wherein the plurality of micro-electrodes is greater than about 3 micro-electrodes.

3. The implant device as in claim 2, wherein the plurality of micro-electrodes is about 4 to about 20 micro-electrodes.

4. The implant device as in claim 1, wherein the multiplexer or switching device comprises a computer chip.

5. The implant device as in claim 4, wherein the power source is a pacemaker.

6. The implant device as in claim 5, wherein the multiplexer or switching device is incorporated into the power source.

7. The implant device as in claim 4, wherein the plurality of micro-electrodes allows the electrical pathway to be directional.

8. A method for clinically effective electrostimulation of neuroglial or neuro-muscular tissue, said method comprising
   (a) positioning an implant device having a distal end and a proximal end such that the distal end can provide electrical stimulation of the neuroglial or neuro-muscular tissue, wherein the distal end of the implant device has a plurality of micro-electrodes and the proximal end of the implant device has an electrical connection terminal for connection to an electrical pulse generator, and wherein various pairs of the micro-electrodes can be electrically connected to the electrical connection terminal,
   (b) positioning the distal end of the implant device sufficiently close to the neuroglial or neuro-muscular tissue to be electrostimulated,
   (c) attaching the electrical pulse generator to the electrical connection terminal of the implant device,
   (d) delivering electrical impulses to the implant device whereby various pairs of the plurality of micro-electrodes can be tested for electrostimulation of the neuroglial or neuro-muscular tissue, and
   (e) selecting a pulsing micro-electrode and a receiving micro-electrode from the various pairs of the plurality of micro-electrodes tested in step (d) to provide clinical effective electrostimulation of the neuroglial or neuro-muscular tissue.

9. The method as in claim 8, wherein the plurality of micro-electrodes is greater than about 3 micro-electrodes.

10. The method as in claim 9, wherein the plurality of micro-electrodes is about 4 to about 20 micro-electrodes.

11. The method as in claim 8, wherein a multiplexer or switching device comprising a computer chip is used to select the pulsing micro-electrode and the receiving micro-electrode in step (e).

12. The method as in claim 11, wherein the power source is a pacemaker.

13. The method as in claim 12, wherein the multiplexer or switching device is incorporated into the power source.

14. The method as in claim 8, wherein the plurality of micro-electrodes allows the electrical pathway to be directional.

15. The method as in claim 8, wherein the clinical effectiveness of the electrostimulation is a clinically significant reduction in the frequency or severity of neurological tremors in the neuroglial or neuro-muscular tissue.

16. A method for clinically effective electrostimulation of gastrointestinal tissue within a patient's endo-abdominal cavity, said method comprising
   (a) inserting an implant device through a trocar into the endo-abdominal cavity, wherein the implant device has a plurality of micro-electrodes and an electrical connection terminal for connection to an electrical pulse generator, wherein various pairs of the micro-electrodes can be electrically connected to the electrical connection terminal,
   (b) positioning the plurality of micro-electrodes within an area of gastrointestinal track to provide electrical stimulation to the gastrointestinal tissue to be electrostimulated,
   (c) immobilizing the implant device so as to maintain good electrical stimulation of the gastrointestinal tissue to be electrostimulated during a treatment regime,
   (d) attaching the electrical pulse generator to the electrical connection terminal of the implant device,
   (e) delivering electrical impulses to the implant device whereby various pairs of the plurality of micro-electrodes can be tested for electrical stimulation of the gastrointestinal tissue to be electrostimulated,
   (f) selecting a pulsing micro-electrode and a receiving micro-electrode from the various pairs of the plurality of micro-electrodes tested in step (e) to provide clinically effective electrical stimulation of the of the gastrointestinal tissue to be electrostimulated, and
   (g) using the selected pulsing micro-electrode and received micro-electrode to electrostimulate the gastrointestinal tissue.

17. The method as in claim 16, wherein the plurality of micro-electrodes is greater than about 3 micro-electrodes.

18. The method as in claim 17, wherein the plurality of micro-electrodes is about 4 to about 20 micro-electrodes.

19. The method as in claim 17, wherein a multiplexer or switching device comprising a computer chip is used to select the pulsing micro-electrode and the receiving micro-electrode in step (f).

20. The method as in claim 19, wherein the power source is a pacemaker.

21. The method as in claim 20, wherein the multiplexer or switching device is incorporated into the power source.

22. The method as in claim 16, wherein the first and second immobilizing mechanisms are tines, clamps, or a flexible attachment member which can be folded back on the elongated body and attached to the elongated body thereby forming a closed loop around the tissue to be treated.

23. The method as in claim 16, wherein the plurality of micro-electrodes allows the electrical pathway to be directional.

24. The method as in claim 16, wherein the gastrointestinal tissue subjected to electrostimulation is associated with the Auerbach plexus or the Meissner plexus.

25. The method as in claim 16, wherein the clinically effective electrical stimulation is designed to effect weight reduction.

26. The method as in claim 24, wherein the clinically effective electrical stimulation is designed to effect weight reduction.

27. A method for clinically effective electrostimulation of gastrointestinal tissue within a patient's endo-abdominal cavity, said method comprising
   (a) implanting an implant device in the endo-abdominal cavity, wherein the implant device has a plurality of micro-electrodes and an electrical connection terminal for connection to an electrical pulse generator, wherein various pairs of the micro-electrodes can be electrically connected to the electrical connection terminal, (b) positioning the plurality of micro-electrodes within an area of gastrointestinal track to provide electrical stimulation to the gastrointestinal tissue to be electrostimulated, (c) immobilizing the implant device so as to maintain good electrical stimulation of the gastrointestinal tissue to be electrostimulated during a treatment regime, (d) attaching the electrical pulse generator to the electrical connection terminal of the implant device, (e) delivering electrical impulses to the implant device whereby various pairs of the plurality of micro-electrodes can be tested, (f) measuring impedance between the various pairs of the plurality of micro-electrodes, (g) selecting a pulsing micro-electrode and a receiving micro-electrode from the various pairs of the plurality of micro-electrodes tested in step (e), wherein the selected pulsing micro-electrode and the selected receiving micro-electrode pair has the lowest, or close to the lowest, impedance measured in step (f), and (h) providing electrostimulation of the gastrointestinal tissue using the selected pulsing micro-electrode and the selected receiving micro-electrode pair.

28. The method as in claim 27, wherein the impedance between the various pairs of the plurality of micro-electrodes is periodically remeasured and the pulsing micro-electrode and the selected receiving micro-electrode pair is reflected based on the remeasured impedance between the various pairs of the plurality of micro-electrodes.

29. The method as in claim 27, wherein the clinically effective electrical stimulation is designed to effect weight reduction.

30. The method as in claim 28, wherein the clinically effective electrical stimulation is designed to effect weight reduction.

31. The method as in claim 28, wherein impedance between the various pairs of the plurality of micro-electrodes is periodically remeasured at least once a day.

32. The method as in claim 28, wherein impedance between the various pairs of the plurality of micro-electrodes is periodically remeasured at least every 12 hours.

33. A method for clinically effective electrostimulation of neuroglial or neuro-muscular tissue, said method comprising (a) positioning an implant device having a distal end and a proximal end such that the distal end can provide electrical stimulation of the neuroglial or neuro-muscular tissue, wherein the distal end of the implant device has a plurality of micro-electrodes and the proximal end of the implant device has an electrical connection terminal for connection to an electrical pulse generator, and wherein various pairs of the micro-electrodes can be electrically connected to the electrical connection terminal, (b) positioning the distal end of the implant device sufficiently close to the neuroglial or neuro-muscular tissue to be electrostimulated, (c) attaching the electrical pulse generator to the electrical connection terminal of the implant device, (d) delivering electrical impulses to the implant device whereby various pairs of the plurality of micro-electrodes can be tested for electrostimulation of the neuroglial or neuro-muscular tissue, and (e) measuring impedance between the various pairs of the plurality of micro-electrodes;

(f) selecting a pulsing micro-electrode and a receiving micro-electrode from the various pairs of the plurality of micro-electrodes tested in step (d), wherein the selected pulsing micro-electrode and the selected receiving micro-electrode pair has the lowest, or close to the lowest, impedance measured in step (e); and (g) providing electrostimulation of the neuroglial or neuro-muscular tissue using the selected pulsing micro-electrode and the selected receiving micro-electrode pair.

34. The method as in claim 33, wherein the impedance between the various pairs of the plurality of micro-electrodes is periodically remeasured and the pulsing micro-electrode and the selected receiving micro-electrode pair is reflected based on the remeasured impedance between the various pairs of the plurality of micro-electrodes.

35. The method as in claim 34, wherein impedance between the various pairs of the plurality of micro-electrodes is periodically remeasured at least once a day.

36. The method as in claim 34, wherein impedance between the various pairs of the plurality of micro-electrodes is periodically remeasured at least every 12 hours.

* * * * *

UNITED STATES PATENT AND TRADEMARK OFFICE
CERTIFICATE OF CORRECTION

| | | |
|---|---|---|
| PATENT NO. | : 7,096,070 B1 | Page 1 of 1 |
| APPLICATION NO. | : 09/777979 | |
| DATED | : August 22, 2006 | |
| INVENTOR(S) | : David Jenkins and Pat Gordon | |

It is certified that error appears in the above-identified patent and that said Letters Patent is hereby corrected as shown below:

Claim 16, Column 18, Line 29 -- After "of the" (first occurrence) delete -- of the -- (second occurrence).

Signed and Sealed this

Twenty-first Day of November, 2006

JON W. DUDAS
*Director of the United States Patent and Trademark Office*